(12) United States Patent
Braithwaite et al.

(10) Patent No.: US 6,845,772 B2
(45) Date of Patent: Jan. 25, 2005

(54) INHALER

(75) Inventors: Philip Braithwaite, Tewkesbury (GB); Steve Williams, Tewkesbury (GB)

(73) Assignee: Innovata Biomed Limited, St. Albans (GB)

( * ) Notice: Subject to any disclaimer, the term of this patent is extended or adjusted under 35 U.S.C. 154(b) by 0 days.

(21) Appl. No.: 10/148,288

(22) PCT Filed: Dec. 1, 2000

(86) PCT No.: PCT/GB00/04623
§ 371 (c)(1),
(2), (4) Date: Sep. 26, 2002

(87) PCT Pub. No.: WO01/39823
PCT Pub. Date: Jun. 7, 2001

(65) Prior Publication Data
US 2003/0116157 A1 Jun. 26, 2003

(30) Foreign Application Priority Data
Dec. 1, 1999 (GB) .............................................. 9928265

(51) Int. Cl.[7] .............................................. A61M 15/00
(52) U.S. Cl. .............................. 128/203.15; 128/203.12; 128/203.23
(58) Field of Search .............................. 604/58–64, 19, 604/186, 246, 94.01; 128/200.14–200.24, 203.12, 203.15, 203.21, 203.22, 203.23, 203.25, 200.13; 222/71, 129, 132, 135, 145.1

(56) References Cited
U.S. PATENT DOCUMENTS

| | | | | |
|---|---|---|---|---|
| 5,002,048 A | * | 3/1991 | Makiej, Jr. ............. | 128/200.23 |
| 5,007,419 A | * | 4/1991 | Weinstein et al. ..... | 128/200.23 |
| 5,437,267 A | * | 8/1995 | Weinstein et al. ..... | 128/200.23 |
| 5,524,613 A | * | 6/1996 | Haber et al. ........... | 128/203.15 |
| 5,575,280 A | * | 11/1996 | Gupte et al. ........... | 128/203.15 |
| 5,664,557 A | * | 9/1997 | Makiej, Jr. ............. | 128/200.23 |
| 5,778,873 A | * | 7/1998 | Braithwaite ............ | 128/203.15 |
| 5,881,719 A | * | 3/1999 | Gottenauer et al. .... | 128/203.15 |
| 6,196,218 B1 | * | 3/2001 | Voges ..................... | 128/200.14 |
| 6,234,167 B1 | * | 5/2001 | Cox et al. .............. | 128/200.14 |
| 6,443,146 B1 | * | 9/2002 | Voges ..................... | 128/200.14 |
| 6,523,536 B2 | * | 2/2003 | Fugelsang et al. ..... | 123/200.14 |
| 6,543,443 B1 | * | 4/2003 | Klimowicz et al. .... | 128/200.23 |
| 6,557,552 B1 | * | 5/2003 | Cox et al. .............. | 128/203.27 |
| 2003/0075172 A1 | * | 4/2003 | Johnson et al. ........ | 128/200.24 |

FOREIGN PATENT DOCUMENTS

| | | | | |
|---|---|---|---|---|
| DE | 2346730 A1 | 4/1975 | | |
| EP | 0539469 B1 | * 4/1995 | .......... | A61M/16/00 |
| WO | WO 92/00771 | 1/1992 | | |
| WO | WO 00/64519 | 11/2000 | | |

* cited by examiner

Primary Examiner—Glenn K. Dawson
(74) Attorney, Agent, or Firm—Bromberg & Sunstein LLP

(57) ABSTRACT

There is described a delivery device which comprises a reservoir, a delivery passage for the delivery of material and a metering member characterised in that the delivery device is provided with a plurality of reservoirs and that the metering member is provided with a plurality of measuring cups adapted to transfer one or more measured doses of material from one or more of the reservoirs to the delivery passage. A method of administering a dry powder and a method and especially a method of treatment of a patient with a bronchial disorder are also described.

20 Claims, 4 Drawing Sheets

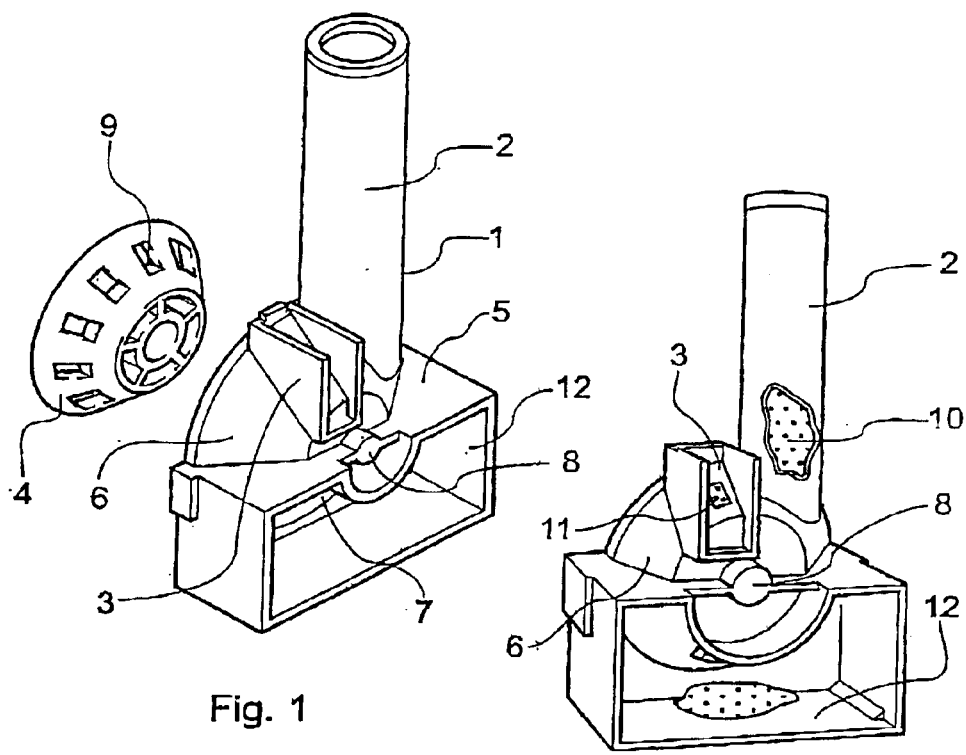
Fig. 1
Fig. 2
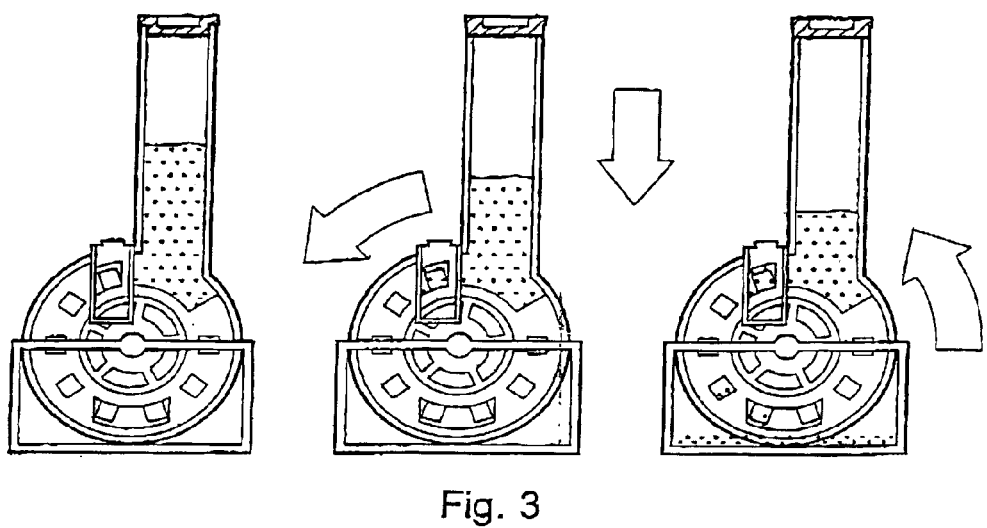
Fig. 3

INHALER

This invention relates to a novel form of material delivery device, for example, a medicament delivery device, such as an inhaler. In particular the invention provides a novel form of dry powder inhaler and a method of delivering a medicament.

Dry powder inhalers are known, such as CLICKHALER, produced by Innovata Biomed in the UK. Such a device is described in European Patent No 0 539 469. Increasingly, patients are required to take more than one medicine and this is no less the case in the treatment of bronchial disorders. Thus, for example, combination therapies such as a steroid with a $\beta_2$ agonist, e.g. fluticasone and salmeterol, have been commercially successful. To date, the administration of such combination therapies comprises the use of a predetermined formulation either as a dry powder, e.g. in a gelatin capsule, or an aerosol. However, this approach suffers from the disadvantage, inter alia, that the medical practitioner is restricted in that it is not possible to vary the quantities of the two medicaments administered. Thus, there has therefore been a long felt need for a dry powder inhalation system which permits the administration of combination therapies.

We have now developed a novel form of medicament delivery device that overcomes or mitigates this problem.

According to the invention we provide a delivery device which comprises a reservoir, a delivery passage for the delivery of material and a metering member characterised in that the delivery device is provided with a plurality of reservoirs and that the metering member is provided with a plurality of measuring cups adapted to transfer one or more measured doses of material from one or more of the reservoirs to the delivery passage.

The device of the invention has utility in a variety of areas, including, for example, medicament delivery. Thus, it is especially suited as an inhaler and especially a dry powder inhaler (DPI).

It is within the scope of this invention for more than two medicaments to be administered, however, it is considered most likely that dual combination therapies would be preferred by the medical profession. Thus the description hereinafter will generally refer to a medicament delivery device adapted to administer a dual combination medicament, but it would be well understood by one skilled in the art that these references could be construed to multiple combinations.

Thus the medicament reservoir preferentially comprises a dual reservoir, the dual reservoir may, for example, comprise a pair of chimneys. Preferentially, each of the reservoirs is a bulk reservoir which supplies a plurality of doses measured by the metering member. The dimensions of the reservoirs may be the same or different depending, inter alia, upon the respective amounts of medicament it is intended to administer. It is important that the two reservoirs are isolated from one another in order to prevent cross contamination of one medicament with the other.

When the delivery device comprises an inhaler, it is preferentially a dry powder inhaler. An example of a conventional inhaler is a CLICKHALER (available from IB) which is provided with a single inhalation passage. However, in the combination therapy inhaler of the invention, the device may be provided with a single or with two inhalation passages.

Thus according to a preferred embodiment of the invention we provide an inhaler which comprises a medicament reservoir, an inhalation passage for the delivery of medicament and a metering member characterised in that the inhaler is provided with a plurality of medicament reservoirs and the metering member is provided with a plurality of measuring cups adapted to transfer one or more measured doses of medicament from one or more of the medicament reservoirs to the inhalation passage.

In one embodiment of the present invention the metering member comprises a frusto conical member analogous to that described in European Patent No 0 539 469. Thus, the metering member may comprise a frusto conical member wherein the side wall of the cone contains one or more measuring chambers. Such a side wall can, preferably, include a plurality of spaced-apart measuring chambers.

The use of the frusto-conical shape in the wall of the metering member containing the measuring chambers allows a good seal to be obtained between the metering member and a seat against which the frusto-conical wall mates.

The metering member is adapted to transfer one or more measured doses of medicament from one or more of the medicament reservoirs to the delivery passage. Therefore, the metering member is preferably provided with dual measuring chambers or a series of dual measuring chambers. As with the conventional CLICKHALER, since the metering member is substantially frusto conical in shape, the measuring chambers are arranged along the outer surface of the side wall of the frusto conical member. Thus, the measuring chambers may form two rows of chambers around the outer surface of the metering member. The measuring chambers in the rows may be aligned to form a plurality of columns of, e.g. two, measuring chambers. Alternatively, the rows may be out of line so that the columns are staggered.

In a further alternative embodiment the metering member may comprise a first and second substantially frusto conical member each of which is provided with a single row of measuring members. In a preferred embodiment the substantially frusto conical members are adjacent to one another and the rows of measuring chambers may be aligned or staggered as with the single frusto conical member device.

When the delivery device comprises separate metering members, it is preferable that they are both frusto conical members. In one embodiment the frusto conical metering members may optionally be positioned with the "closed" frusto conical ends facing or alternatively, with the "open" ends facing.

As with the CLICKHALER described in the prior art patent, the frusto conical metering member is rotatable about a central axis. When the delivery device of the invention comprises two separate metering members then they will generally be aligned along the same axis. However, the axle about which they actually rotate may be the same, i.e. is a shared axle or they may be provided with separate axles.

The delivery device of the invention may be adapted so as to comprise a first, substantially conventional device, e.g. in the case of an inhaler, a CLICKHALER, which is provided with means to attach a second delivery device to it. Preferably, the second delivery will be a "clip on" device. Thus the first delivery device may be provided with means to receive a second deliver device. Although a number of means of attachment can be contemplated, one embodiment is for the first and second delivery devices to be provided with one or more tabs of, e.g. a resilient plastics material wherein the tab on the first delivery device is adapted to engage the tab on the second delivery device. Preferably each of the first and second delivery devices are provided with a plurality of tabs. In a further embodiment a conventional delivery device, e.g. an inhaler, may be provided with an adapter which is capable of engaging with a first and a second delivery device.

In the conventionally known CLICKHALER a medicament pocket is provided adjacent the measuring chamber when the metering member is in the medicament delivery position. The medicament pocket forms a conduit between the measuring chamber and the inhalation passage. Generally, the medicament pocket is aligned to be coplanar with the axis of rotation of the metering member. In the combination therapy inhaler of the invention, there are two medicament pockets provided. Thus, it is within the scope of this invention for the medicament pockets to be aligned coplanar with the axis of rotation of the metering member. However, a slimmer device is produced if the medicament pockets are aligned perpendicular to the axis of rotation.

Thus, in operation, the device may be moved to a first position in which the first medicament is transferred to a first measuring chamber in the metering member. The device is then moved to a second position in which a second medicament is transferred from a second measuring chamber. Then either separately or together the metering members are rotated to a third position where medicament is delivered to the delivery passage.

The dispensing member may be a conventionally known member such as a frusto conical member described herein and in EP 0 539 469 and may optionally be provided with a moisture resistant sleeve and/or be provided with an air inlet. An air inlet is especially suited when the delivery device is an inhaler.

The delivery device of the invention is advantageous in that, inter alia, it may operate by the administration of a plurality of medicaments at the same time, sequentially or at different times, e.g. a first medicament being administered in the morning and a second medicament in the afternoon.

A variety of medicaments may be administered by using the inhaler of the invention. Such medicaments are generally antibiotics, bronchodilators or other anti-asthma drugs. Such medicaments include, but are not limited to $\beta_2$-agonists, e.g. fenoterol, formoterol, pirbuterol, reproterol, rimiterol, salbutamol, salmeterol and terbutaline; non-selective beta-stimulants such as isoprenaline; xanthine bronchodilators, e.g. theophylline, aminophylline and choline theophyllinate; anticholinergics, e.g. ipratroplum bromide; mast cell stabilisers, e.g. sodium cromoglycate and ketotifen; bronchial anti-inflammatory agents, e.g. nedocromil sodium; and steroids, e.g. beclomethasone dipropionate, fluticasone, budesonide and flunisolide; and combinations thereof.

Specific combinations of medicaments which may be mentioned include combinations of steroids, such as, beclomethasone dipropionate, fluticasone, budesonide and flunisolide; and combinations of to $\beta_2$-agonists, such as, formoterol and salmeterol. It is also within the scope of this invention to include combinations of one or more of the aforementioned steroids with one or more of the aforementioned $\beta_2$-agonists.

Further medicaments which may be mentioned include systemically active materials, such as, proteinaceous compounds and/or macromolecules, for example, hormones and mediators, such as insulin, human growth hormone, leuprolide and alpha interferon; growth factors, anticoagulants, immunomodulators, cytokines and nucleic acids.

By the term dry powder we mean a medicament in finely divided form.

The invention will now be described by way of example only and with reference to the accompanying drawings in which:

FIG. 1 is a perspective view of a prior art inhaler;

FIG. 2 is a partially cut away perspective view of a prior art inhaler;

FIG. 3 is a schematic representation of the sequence of operation of a prior art inhaler;

Figure 4:
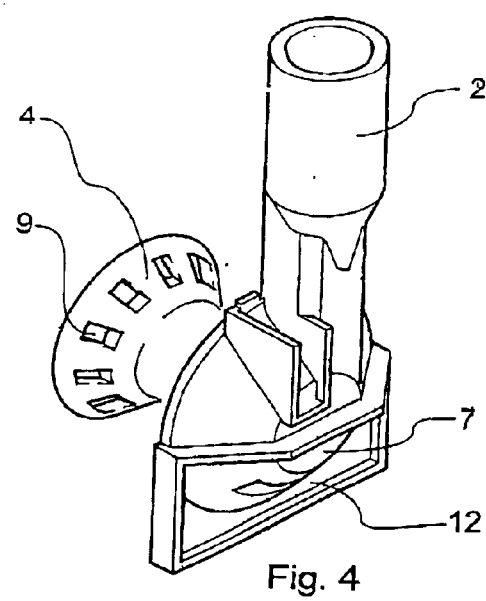
FIG. 4 is a perspective view of a prior art inhaler.
Figure 5:
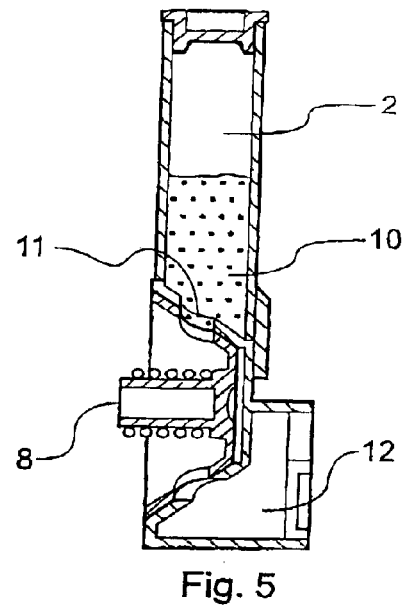
FIG. 5 is a cross-sectional view of a prior art inhaler.

Referring to FIGS. 1 to 5, a dry powder inhaler (1) comprises a medicament reservoir (2), a medicament pocket (3) and a metering member (4). A medicament pocket (3) is connected to the medicament reservoir (2) by a reservoir support (5) and is itself connected to recess (6) which is provided with a back plate (7) for a seat for the frusto conical metering member (4). The medicament pocket forms a conduit between the metering member (4) and the inhalation passage (not shown). The metering member (4) is rotatable about an axis (8). The metering member (4) is provided with a row of measuring cups (9) (also known as dispensing cups). The measuring cups (9) are dimensioned so as to measure a predetermined amount of medicament (10). In operation, medicament (10) is dispensed from the reservoir (2) into the measuring cup (9). The metering member is rotated (in an anti-clockwise direction) thus bringing the full measuring cup (11) into line with the medicament pocket (3). After inhalation of the medicament by the patient, the metering member (4) is further rotated to bring the measuring cup into the dump box (12) in an essentially inverted or upside down position allowing any residual medicament in the measuring cup (9) to be emptied into the dump box (12).

Figure 6:
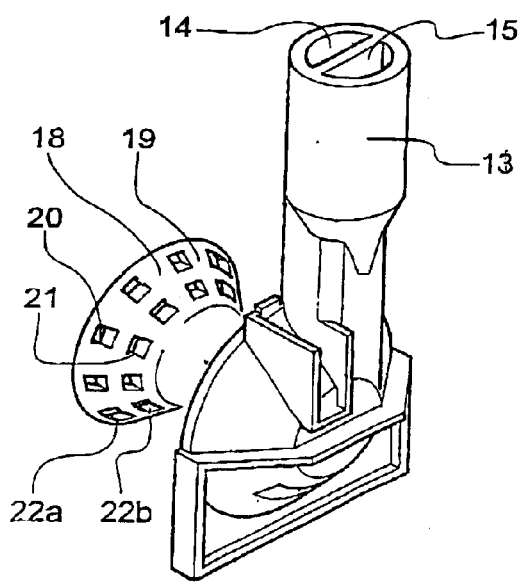
FIG. 6 is a perspective view of an inhaler of the invention with two rows of measuring cups in a single frusto conical member.
Figure 7:
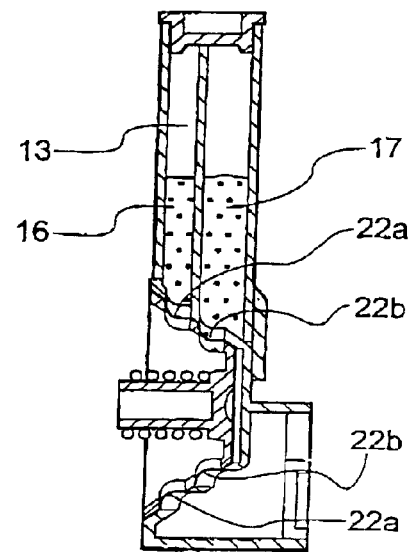
FIG. 7 is a cross-sectional view of the inhaler of FIG. 6.

Referring now to FIGS. 6 and 7. A combination therapy inhaler (13) of the invention is provided with two medicament reservoirs (14 and 15) containing a first (16) and second (17) medicament. A metering member (18) comprises an essentially frusto conical member. The side wall (19) of the frusto conical member (18) is provided with two rows (20 and 21) of measuring cups (22). In the embodiment shown, the two rows (20 and 21) of measuring cups (22) are aligned so as to form columns (23) of measuring cups (22a and 22b). In operation measuring cup (22a) is filled with a first medicament from reservoir (14) and measuring cup (22b) is fitted with a second medicament from reservoir (15). The metering member (18) is then rotated in an analogous fashion to the prior art device.

Figure 8:
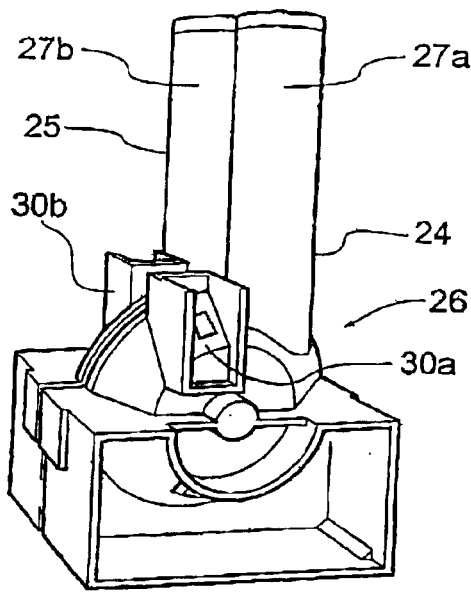
FIG. 8 is a perspective view of an inhaler of the invention with two frusto conical members.
Figure 9:
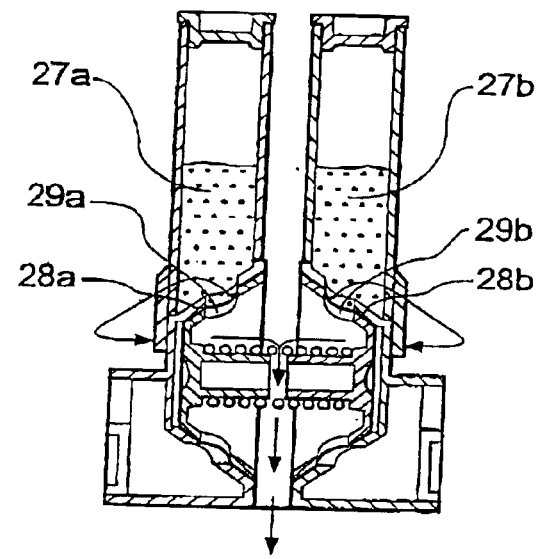
FIG. 9 is a cross-sectional view of the inhaler of FIG. 8.
Figure 10:
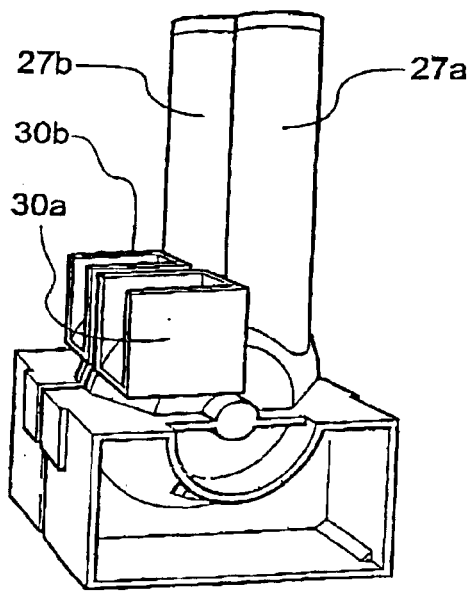
FIG. 10 is a perspective view of an inhaler of the invention provided with medicament pockets aligned perpendicular to the axis of rotation of the metering member.

Referring to FIGS. 8 to 10. A first inhaler (24) resembles that of the prior art. A second inhaler (25) also resembling that of the prior art is clipped onto the first to produce an inhaler (26) comprising two medicament reservoirs (27a and 27b) two metering members (28a and 28b) each provided with a single row of measuring cups (29a and 29b respectively) and two medicament pockets (30a and 30b). The metering members (28) operate similar fashion to the prior art. Metering member (28a) may be operated in conjunction with or independent of metering member (28b).

In FIG. 10 the medicament pocket (30a and 30b) are arranged perpendicular to the axis of rotation of the metering members (28a and 28b) allowing a slimmer device to be produced.

Figure 11:
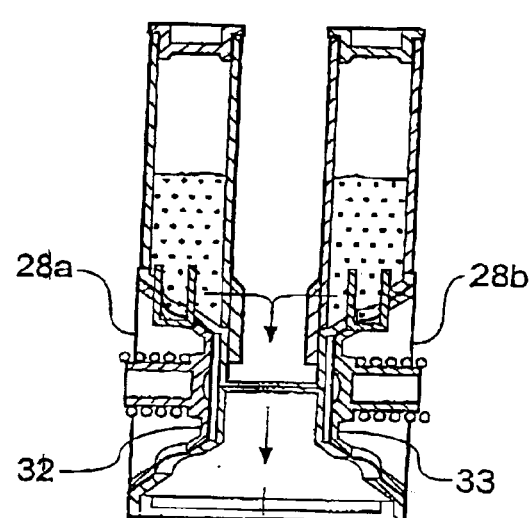
FIG. 11 is a cross sectional view of an inhaler with the closed ends of the frusto conical metering members facing.

Referring to FIG. 11. An inhalation device is provided with two metering members (28a and 28b). The closed ends (32 and 33) face each other.

A variety of mechanisms may be used for the operation of the inhaler. One preferred mechanism is for movement from the closed to the measuring position to be achieved by removal of a mouth piece which is operably linked to the moisture resistor. Movement from the measuring position to the transitory position would use a mechanism similar to that described in EP 0 539 469, e.g. by depressing the button half way. Movement to the transfer position being achieved by further depressing the button, and then depression completely, moving the metering cone and the moisture resistor to the delivery position.

Figure 12:
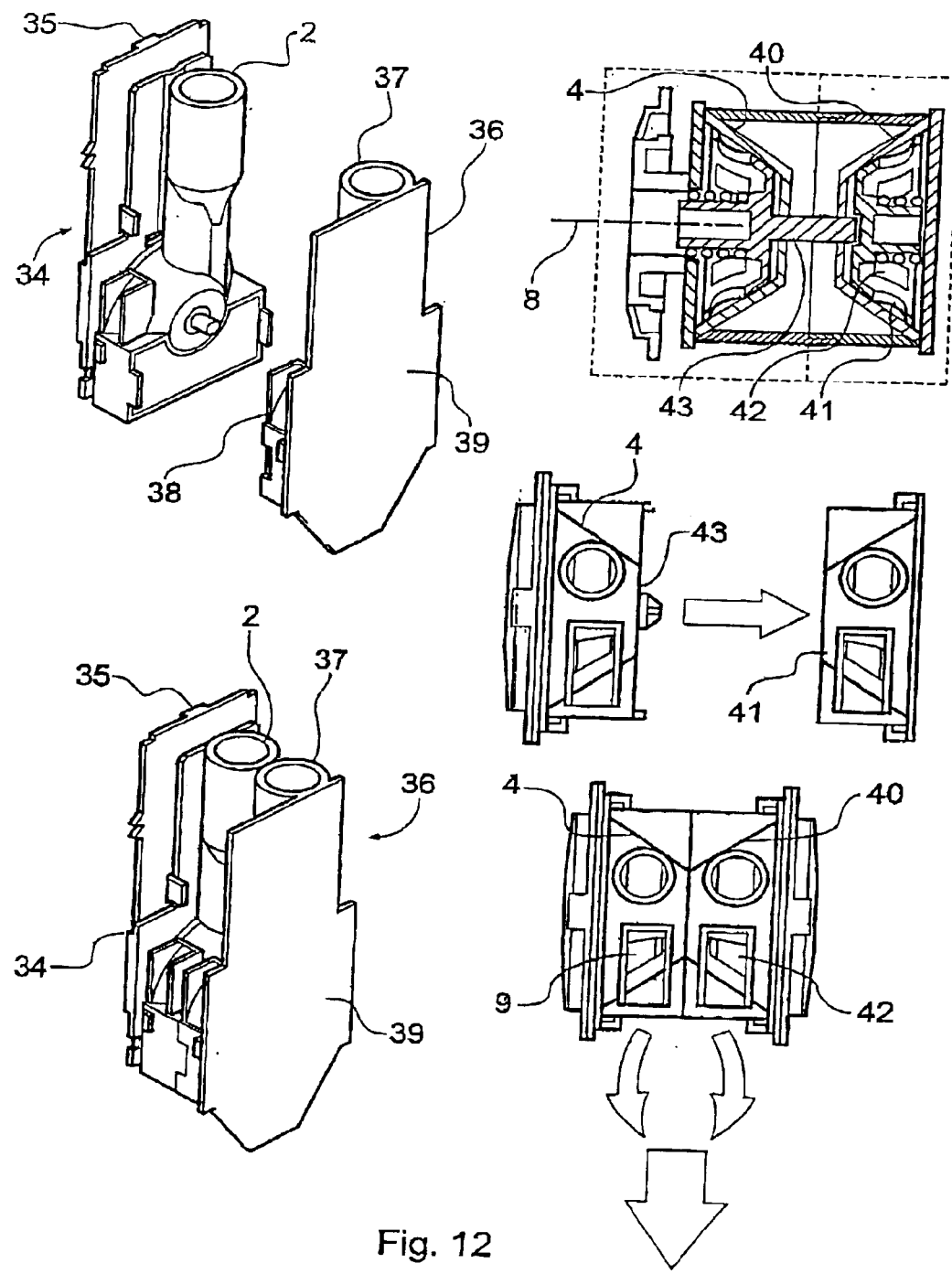
FIG. 12 is a perspective view of a CLICKHALER provided with a "clip on" combination attachment.

Referring to FIG. 12. An inhalation device comprises a master system (34) comprising an actuator (35), a medicament reservoir (2) and a dosage counter (not shown). The device is provided with a secondary system (36) comprising its own medicament reservoir (37), an inhalation passage (38) and a backplate (39). The secondary system (6) is provided with a metering member (40) being a frusto conical member (41) with measuring cups (42). The metering member (40) is aligned coaxially with the metering member (4) of the master system. The metering member (4) is provided with an axial linking member (43). The linking member (43) sits on the axis of rotation (8) of metering member (4) and is adapted to drivably engage axially with metering member (40). Thus, in use, depression of the actuator (35) on the master system rotates both metering members (4 and 40) causing medicament to be dispensed from each medicament reservoir (2 and 37) into the respective measuring cups (9 and 42). The two medicaments, which may be the same or different, mix in the inhalation passage, before being inhaled by the patient.

What is claimed is:

1. A delivery device which comprises a plurality of reservoirs, two delivery passages for the delivery of material and a metering member, wherein the metering member is a frusto conical member provided with a plurality of measuring cups adapted to transfer one or more measured doses of material from one or more of the reservoirs to the delivery passages.

2. A delivery device according to claim 1 characterised in that the plurality of reservoirs comprises a dual reservoir.

3. A delivery device according to claim 1 characterised in that the plurality of reservoirs comprises a bulk reservoir.

4. A delivery device according to claim 1 characterised in that the material is a medicament.

5. A delivery device according to claim 4 characterised in that the medicament is a dry powder.

6. A delivery device according to claim 4 characterised in that the device is an inhaler.

7. A delivery device according to claim 6 characterised in that the inhaler is a dry powder inhaler.

8. A delivery device according to claim 1 characterized in that the metering member is adapted to transfer a plurality of measured doses of medicament from the plurality of medicament reservoirs to an inhalation passage.

9. A delivery device according to claim 1 characterised in that the metering member is provided with a dual set of measuring cups.

10. A delivery device according to claim 1 characterised in that the measuring cups form two rows of chambers around the outer surface of the metering member.

11. A delivery device according to claim 10 characterised in that the measuring cups in the rows are aligned to form columns each comprising two measuring cups.

12. A delivery device according to claim 1 characterised in that the metering member comprises a first and second substantially frusto conical member each of which is provided with a single row of measuring cups.

13. A delivery device according to claim 12 characterised in that the substantially frusto conical members are adjacent to one another and the rows of measuring cups are aligned.

14. A delivery device according to claim 12 characterised in that the frusto conical metering members are positioned with the closed frusto conical ends facing each other.

15. A delivery device according to claim 12 characterised in that the open ends facing each other.

16. A delivery device according to claim 12 characterised in that the first and second substantially frusto conical members are each rotatable about separate axles.

17. A delivery device according to claim 1 characterised in that metering member is rotatable about a central axis.

18. A delivery device according to claim 1 characterised in that the measuring cups are aligned coplanar with an axis of rotation of the metering member.

19. A delivery device according to claim 1 characterised in that the measuring cups are aligned perpendicular to an axis of rotation.

20. A delivery device, according to claim 1 characterised in that it is adapted to operate by the administration of a plurality of medicaments at the same time.

\* \* \* \* \*